United States Patent [19]

Miyano et al.

[11] Patent Number: 5,998,635
[45] Date of Patent: Dec. 7, 1999

[54] PROCESS FOR PRODUCING A β-LACTONE DERIVATIVE

[75] Inventors: Sotaro Miyano; Tetsutaro Hattori; Yutaka Suzuki; Shuichi Oi, all of Sendai; Takashi Miura; Tsutomu Hashimoto, both of Hiratsuka, all of Japan

[73] Assignee: Takasago International Corporation, Tokyo, Japan

[21] Appl. No.: 09/265,694

[22] Filed: Mar. 10, 1999

[30] Foreign Application Priority Data

Mar. 11, 1998 [JP] Japan ................................. 10-059522

[51] Int. Cl.$^6$ ................................................. C07D 305/12
[52] U.S. Cl. ................................................................ 549/329
[58] Field of Search ................................................ 549/329

[56] References Cited

U.S. PATENT DOCUMENTS 2,763,644  9/1956  Donaruma ........................... 260/239.3

OTHER PUBLICATIONS

The Chemical Society of Japan, 74$^{th}$ Spring Annual Convention, Mar. 27, 1998–Mar. 30, 1998; Proceedings of Lectures II, 1C309 and 1C310, (with partial English translation).

Harold E. Zaugg, Organic Reactions, Beta–Lactones, vol. 8, 1954, pp. 305–363.

Yan Zhang, et al., Marcomolecules, "Stereochemistry of the Ring–Opening Polymerization of (S)–Beta–Butyrolactone," 1990, vol. 23, pp. 3206–3212.

Toshio Sato, et al., Tetrahedron Letters, "A Novel Synthetic Method for Optically Active Terpenes by the Ring–Opening Reaction of (R)–(+)–Beta–Methyl–Beta–Propiolactone," vol. 21, 1980, pp. 3377–3380.

Waldemar Adam, et al., Journal of the American Chemical Society, "Stereospecific Introduction of Double Bonds via Thermolysis of Beta–Lactones," vol. 94, Mar. 22, 1972, pp. 2000–2006.

T. Howard Black, et al., J. Org. Chem., Dyotropic Rearrangement of Cycloalkyl Beta–Lactones. Formation of Spiro vs Fused Butyrolactones as a Function of Ring Size, vol. 53, 1988, pp. 5922–5927.

William J. Evans, et al., J. Am. Chem. Soc., "Synthesis and Structure of the Polymetallic Yttrium Alkoxide Complex $Y_3(\mu_3–OCMe_3)(\mu_3–Cl)(\mu–OCMe_3)_3(OCMe_3)_4(THF)_2$ and Related Complexes: $Ln_3(\mu_3–OR)(\mu_3–X)(\mu–OR)_3$ Building Blocks in Yttrium and Lanthanide Alkoxide Chemistry," vol. 110, 1988, pp. 1841–1850.

Julian A. Davies, et al., J. Chem. Soc., Dalton Trans., "Hard Ligands as Donors to Soft Metals. Part 3. Cationic Bix(solvent) Complexes of Palladium (II); Cations for Catalysts," 1980, pp. 2246–2249.

Shuichi Oi, et al., Tetrahedron Letters, "Cationic Palladium(II) Complex–Catalyzed Hetero Diels–Alder Reaction of Dienes with Aldehydes," vol. 37, No. 35, 1996, pp. 6351–6354.

*Primary Examiner*—Ba K. Trinh
*Attorney, Agent, or Firm*—Oblon, Spivak, McClelland, Maier & Neustadt, P.C.

[57] ABSTRACT

The present invention provides a process for producing a β-lactone derivative by reacting an aldehyde represented by formula (1):

RCHO    (1)

wherein R represents a C1–C15 alkyl group which may be substituted by an aryl group, a C2–C15 alkenyl group, a 5–7-membered alicyclic group, or a phenyl group which may be substituted by a C1–C4 alkyl group; and ketene in the presence of a transition metal-phosphine complex. An industrially valuable β-lactone can be efficiently produced at high yield.

4 Claims, No Drawings

PROCESS FOR PRODUCING A β-LACTONE DERIVATIVE

BACKGROUND OF THE INVENTION

1 Field of the Invention

The present invention relates to a process for producing a β-lactone derivative which is useful as a starting material for polymers, an intermediate in the field of organic synthetic chemicals, a starting material for medicaments, and the like.

2 Background Art

Conventionally, there are known the following processes for producing a β-lactone derivative:

(1) a method described by H. E. Zaugg in *Organic Reactions*, Vol. 8, pp. 305–363 (1954) wherein ketene and an aldehyde are reacted in the presence of a Lewis acid catalyst such as a halide of boron, zinc, aluminum, titanium, or iron or an organic complex of the halide;

(2) a method disclosed in Japanese Patent Publication (kokoku) No. 47-25065 wherein a ketene and an aliphatic aldehyde are reacted in the presence of tetrahydrofuran together with boron trifluoride and/or a complex thereof;

(3) a method disclosed in Japanese Patent Application Laid-Open (kokai) Nos. 46-51422, 48-61420, and 48-64019 wherein a ketene and an aliphatic aldehyde are reacted in the presence of a boron trifluoride-ether complex as a catalyst;

(4) a method disclosed in U.S. Pat. No. 2,763,644 wherein 4-methylene-2-oxetane, also called diketene, is hydrogenated in the presence of palladium black;

(5) a method described by Y. Zhang et al. in *Macromolecules*, Vol. 23, pp. 3206–3212 (1990) wherein a hydroxyl group of a 3-hydroxycarboxylate ester is mesylated with methanesulfonyl chloride, the resultant ester is hydrolyzed, and the hydrolysate is cyclized with sodium hydrogencarbonate;

(6) a method described by T. Sato et al. in *Tetrahedron Lett.*, Vol. 21, pp. 3377–3380 (1980) wherein a 3-bromocarboxylic acid derivative is cyclized with sodium carbonate; and (7) a method described by W. Adam et al. in *J. Am. Chem. Soc.*, Vol. 94, pp. 2000–2006 (1972) or described by T. H. Black et al. in *J. Org. Chem.*, Vol. 53, pp. 5922–5927 (1988) wherein a β-hydroxycarboxylic acid derivative is cyclized by the treatment with benzenesulfonyl chloride in the presence of pyridine.

However, processes for producing a β-lactone derivative which have been reported so far are not satisfactory, and have problems described below.

For example, in the process (1), since catalysts do not necessarily show the same activity in various condensation reactions, a suitable catalyst must be selected in accordance with the target β-lactone. The process (2) has limitation on reaction conditions such as a constant mol ratio of the aldehyde to ketene of 1.0/0.9 or constant reaction temperature of 10–15° C. The process (3) provides poor yield of a β-lactone derivative. The process (4) is not suited for producing a typical β-lactone derivative, since the product is limited to 4-methyl-2-oxetanone. The processes (5) to (7) require intricate procedures for preparing starting materials.

SUMMARY OF THE INVENTION

In order to solve the aforementioned problems, an object of the present invention is to provide a process for producing a β-lactone derivative with high efficiency.

The present inventors have conducted earnest studies, and have found that when an aldehyde and ketene are reacted in the presence of a transition metal-phosphine complex, a β-lactone derivative is produced at high efficiency. The present invention has been accomplished based on this finding.

Accordingly, in the present invention, there is provided a process for producing a β-lactone derivative represented by the following formula (3):

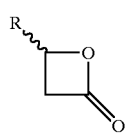

(3)

wherein R represents a C1–C15 alkyl group which may be substituted by an aryl group, a C2-C15 alkenyl group, a 5–7 membered alicyclic group, or a phenyl group which may be substituted by a C1–C4 alkyl group; which process comprising the step of reacting an aldehyde represented by the following formula (1)

RCHO   (1)

Wherein R represents the same as def inied above; and ketene represented by formula (2):

$CH_2=C=O$   (2)

in the presence of, as a catalyst, a transition metal-phosphine complex.

According to the present invention, a β-lactone derivative can be produced at high yield through reaction of an aldehyde and ketone in the presence of a transition metal-phosphine complex. The β-lactone derivative is useful as a starting material for polymers, an intermediate in the field of organic synthetic chemicals, and the like.

BEST MODES FOR CARRYING OUT THE INVENTION

In the aldehyde represented by the above-described formula (1), R represents a C1–C15 alkyl group which may have an aromatic ring, a C2–C15 alkenyl group, a 5–7-membered alicyclic group, or a phenyl group which may be substituted by a C1–C4 alkyl group, in which the aromatic ring is preferably a C6–C10 aromatic hydrocarbon, more preferably benzene or naphthalene. Examples of the aldehyde include those in which R is a C1–C15 alkyl group which may have an aromatic ring, such as acetaldehyde, propylaldehyde, n-butylaldehyde, 2-methylpropylaldehyde, n-valeroaldehyde, 2-methylbutylaldehyde, isovaleroaldehyde, 2,2-dimethylpropylaldehyde, n-hexylaldehyde, 2-methylvaleroaldehyde, 3-methylvaleroaldehyde, 4-methylvaleroaldehyde, 2,2-dimethylbutylaldehyde, 2,3-dimetylbutylaldehyde, 3,3-dimetylbutylaldehyde, n-heptylaldehyde, 2-metylhexylaldehyde, 2-ethylvaleroaldehyde, 2-propylbutylaldehyde, 3-ethylvaleroaldehyde, 3-methylhexylaldehyde, 4-methylhexylaldehyde, 5-methylhexylaldehyde, 2,2-dimethylvaleroaldehyde, 2,3-dimethylvaleroaldehyde, 2,4-dimethylvaleroaldehyde, 3,3-dimethylvaleroaldehyde, 3,4-dimethylvaleroaldehyde, 4,4-dimethylvaleroaldehyde, 2,2,3-trimethylbutylaldehyde, 2,3,3-trimethylbutylaldehyde, n-octylaldehyde, 2-methylheptylaldehyde, 3-methyheptylaldehyde, 4-methylheptylaldehyde, 5-methylheptylaldehyde, 6-methylheptylaldehyde, 2-ethylhexylaldehyde, 3-ethylhexylaldehyde, 4-ethylhexylaldehyde, 2-propylvaleroaldehyde, 2,2-dimethylhexylaldehyde, 2,3-dimethylhexylaldehyde, 2,4-dimethylhexylaldehyde, 2,5-dimethylhexylaldehyde, 3,3-dimethylhexylaldehyde, 3,4-dimethylhexylaldehyde, 3,5-dimethylhexylaldehyde, 4,4-dimethylhexylaldehyde, 4,5-dimethylhexylaldehyde, 5,5-dimethylhexylaldehyde, n-nonylaidehyde, 2-methyloctylaldehyde, 3-methyloctylaldehyde, 4-methyloctylaldehyde, 5-methyloctylaldehyde, 6-methyloctylaldehyde, 7-methyloctylaldehyde, 2-ethylheptylaldehyde, 3-ethylheptylaldehyde, 4-ethylheptylaldehyde, 5-ethylheptylaldehyde, 2-propylhexylaldehyde, 3-propylhexylaldehyde, 2,2-dimethylheptylaldehyde, 2,3-dimethylheptylaldehyde, 2,4-dimethylheptylaldehyde, 2,5-dimethylheptylaldehyde, 2,6-dimethylheptylaldehyde, 3,3-dimethylheptylaldehyde, 3,4-dimethylheptylaldehyde, 3,5-dimethylheptylaldehyde, 3,6-dimethylheptylaldehyde, n-decylaldehyde, 2-methylnonylaldehyde, 3-methylnonylaldehyde, 4-methylnonylaldehyde, 5-methylnonylaldehyde, 6-methylnonylaldehyde, 7-methylnonylaldehyde, 8-methylnonylaldehyde, 2-ethyloctylaldehyde, 3-ethyloctylaldehyde, 4-ethyloctylaldehyde, 5-ethyloctylaldehyde, 6-ethyloctylaldehyde, 2-propylheptylaldehyde, 3-propylheptylaldehyde, 4-propylheptylaldehyde, 2,2-dimethyloctylaldehyde, 2,3-dimethyloctylaldehyde, 2,4-dimethyloctylaldehyde, n-undecylaldehyde, n-dodecylaldehyde, n-tridecylaldehyde, n-tetradecylaldehyde, or n-pentadecylaldehyde, phenylethylaldehyde, phenylpropylaldehyde, phenylbutylaldehyde, phenylpentylaldehyde, phenylhexylaldehyde, phenylheptylaldehyde, phenyloctylaldehyde, phenylnonylaldehyde, phenyldecylaldehyde, phenylundecylaldehyde, phenyldodecylaldehyde, phenyltridecylaldehyde, phenyltetradecylaldehyde, phenylpentadecylaldehyde; aldehydes in which R is a C2–C15 alkenyl group, such as acrylaldehyde, 2-butenal, 3-butenal, 2-pentenal, 3-pentenal, 4-pentenal, 2-hexenal, 3-hexenal, 4-hexenal, 5-haxenal, heptenal, octenal, nonenal, decenal, undecenal, dodecenal, tridecenal, tetradecenal, pentadecenal; aldehydes in which R is a 5–7-membered alicyclic group, such as cyclopentylaldehyde, cyclohexylaldehyde, or cycloheptylaldehyde; and aldehydes in which R is a phenyl group which may be substituted by a C1–C4 alkyl group, such as benzaldehyde, tolylcarbardehyde, xylylcarbardehyde, cumylcarbardehyde, or 4-tert-butylphenylcarbardehyde.

No particular limitation is imposed on the process for producing ketene represented by the above-described formula (2); ketene may be prepared by heating acetone according to a method described by W. J. Evans et al. in *J. Am. Chem. Soc.*, Vol. 110, pp. 1841 (1988).

Examples of the transition metal-phosphine complex include a phosphine complex of a transition metal such as rhodium, ruthenium, palladium, iridium, nickel, or platinum, with a palladium-phosphine complex and a platinum-phosphine complex being preferred. Of these, there is preferably used a transition metal-phosphine complex represented by the following formula (4):

[ML$_n$X$_2$]Y$_2$     (4)

wherein M represents palladium or platinum; L represents a tertiary phosphine; X represents a C1–C5 alkylnitrile, benzonitrile, phthalonitrile, pyridine, dimethyl sulfoxide, N,N-dimethylformamide, or acetone; Y represents a halogen atom, BF$_4$, ClO$_4$, CF$_3$SO$_3$, PF$_6$, or BPh$_4$; Ph represents a phenyl group; and n is 2 when L is a monodentate phosphine ligand and 1 when L is a bidentate phosphine ligand.

The tertiary phosphine represented by L in the above-described formula (4) may be a monodentate phosphine ligand or a bidentate phosphine ligand. Examples of the monodentate phosphine ligand include trialkylphosphines such as triethylphosphine or tributylphosphine and triarylphosphines such as triphenylphosphine or tri(tolyl) phosphine, and examples of the bidentate phosphine ligand include dppe (1,2-bis(diphenylphosphino)ethane), dppp (1,3-bis(diphenylphosphino)propane), dppb (1,4-bis (diphenylphosphino)butane), dppf (1,1'-bis (diphenylphosphino)ferrocene), BINAP (2,2'-bis (diphenylphosphino)-1,1'-binaphthyl), and T-BINAP (2,2'-bis(ditolylphosphino)-1,1'-binaphthyl) and a bidentate phosphine ligand being preferred.

In the formula (4), X is a C1–C5 alkylnitrile, benzonitrile, phthalonitrile, pyridine, dimethyl sulfoxide, N,N-dimethylformamide, or acetone, with acetonitrile and benzonitrile being preferred. Examples of the C1–C5 alkylnitrile include acetonitrile, propionitrile, butyronitrile, valeronitrile, isovaleronitrile, and pivalonitrile. In the formula (4), Y represents a halogen atom, BF$_4$, ClO$_4$, CF$_3$SO$_3$, PF$_6$, or BPh$_4$, with BF$_4$ and ClO$_4$ being preferred. Examples of the halogen atom include a fluorine atom, a chlorine atom, a bromine atom, and an iodine atom.

Preferable examples of the transition metal-phosphine complex represented by the above-described formula (4) include bis(benzonitrile)-bis(triphenylphosphine)palladium bis(tetrafluoroborate) ([Pd(PPh$_3$)$_2$(PhCN)$_2$](BF$_4$)$_2$), bis (benzonitrile)-1,2-bis(diphenylphosphino)ethanepalladium bis(tetrafluoroborate) ([Pd(dppe)(PhCN)$_2$](BF$_4$)$_2$), bis (benzonitrile)-1,3-bis(diphenylphosphino) propanepalladium bis(tetrafluoroborate) ([Pd(dppp)(PhCN) $_2$](BF$_4$)$_2$), bis(benzonitrile)-1,4-bis(diphenylphosphino) butanepalladium bis(tetrafluoroborate) ([Pd(dppb)(PhCN)$_2$] (BF$_4$)$_2$), bis(benzonitrile)-1,1'-bis(diphenylphosphino) ferrocenepalladium bis(tetrafluoroborate) ([Pd(dppf)(PhCN) $_2$](BF$_4$)$_2$), bis(benzonitrile)-2,2'-bis(diphenylphosphino)-1, 1'-binaphthylpalladium bis(tetrafluoroborate) ([Pd(BINAP) (PhCN)$_2$](BF$_4$)$_2$), and bis(benzonitrile)-2,2'-bis (diphenylphosphino)-1,1'-binaphthylplatinum bis (tetrafluoroborate) ([Pt(BINAP)(PhCN)$_2$](BF$_4$)$_2$).

No particular limitation is imposed on the process for producing the transition metal-phosphine complex represented by the above-described formula (4); it may be prepared according to a method described by S. G. Murray at al. in *J. Chem. Soc. Dalton Trans.*, pp. 2246–2249 (1980); a method described by S. Oi et al. in *Tetrahedron Letters*, Vol. 37, pp. 6351–6354 (1996), or another method based on the two methods.

In order to carry out the process according to the present invention, the above-described aldehyde (1) and a transition metal-phosphine complex are dissolved in an organic solvent, to form a solution. Ketene is added to the solution, and the mixture is allowed to react. The operations are conducted under an atmosphere comprising an inert gas such as argon or-nitrogen.

The transition metal-phosphine complex serving as a catalyst is used in an amount of 0.001–0.2 times (by mol) that of the aldehyde (1) serving as a starting material, preferably 0.005–0.1 times.

No particular limitation is imposed on the organic solvent which is used in the present invention so long as it is in the form of a liquid at the reaction temperature. A solvent such as an aprotic solvent is preferred and examples thereof include a halogenated hydrocarbon such as methylene chloride or chloroform; an aromatic hydrocarbon such as benzene or toluene; an ester such as ethyl acetate or butyl acetate; and an ether such as tetrahydrofuran or dimethoxyethane. Of these, an aromatic hydrocarbon such as benzene or toluene and a halogenated hydrocarbon such as methylene chloride or chloroform are particularly preferred.

The aldehyde (1) is generally used in an amount of 1 mol/L–0.01 mol/L based on the amount of an organic solvent, preferably 0.2 mol/L–0.02 mol/L.

Although the reaction according to the present invention may be carried out within a temperature range from −78° C. to room temperature, it is preferably carried out within a temperature range from 0° C. to room temperature in view of high yield of the product. The reaction time is preferably 0.5–10 hours.

When the reaction is completed, acid such as diluted hydrochloric acid is added to the reaction mixture. The product is extracted with an organic solvent which is used in the reaction or an organic solvent such as ethyl acetate or butyl acetate, and washed with water. The resultant organic phase is optionally dried, and subjected to further purification procedures such as filtration, concentration, and distillation, to thereby purify and isolate a β-lactone derivative (3) as a target substance of the present invention.

EXAMPLES

The present invention will next be described in detail by way of examples, which should not be construed as limiting the invention thereto. The following methods and instruments were used for the measurements.

Infrared Absorption Spectrometry (IR): FTIR-8300, IR-460 (Shimadzu Corp.)

$^1$H-Nuclear Magnetic Resonance Spectrometry ($^1$H-NMR): AC-250, DPX-400 (Brooker Co.)

Internal Standard: tetramethylsilane

Gas Chromatography: GC-14A (Shimadzu Corp.)

Column: CROMPACK (0.25 mm ID×25 m) (Crompack Co.)

The phosphine complexes used herein may also be referred to as the following abbreviations:

[Pd(PPh$_3$)$_2$(PhCN)$_2$](BF$_4$)$_2$:
bis(benzonitrile)-bis(triphenylphosphine)palladium bis(tetrafluoroborate);

[Pd(dppe)(PhCN)$_2$](BF$_4$)$_2$:
bis(benzonitrile)-1,2-bis(diphenylphosphino)ethanepalladium bis(tetrafluoroborate);

[Pd(dppp)(PhCN)$_2$](BF$_4$)$_2$:
bis(benzonitrile)-1,3-bis(diphenylphosphino)propanepalladium bis(tetrafluoroborate);

[Pd(dppb)(PhCN)$_2$](BF$_4$)$_2$:
bis(benzonitrile)-1,4-bis(diphenylphosphino)butanepalladium bis(tetrafluoroborate);

[Pd(dppf)(PhCN)$_2$](BF$_4$)$_2$:
bis(benzonitrile)-1,1'-bis(diphenylphosphino)ferrocenepalladium bis(tetrafluoroborate);

[Pd(BINAP)(PhCN)$_2$](BF$_4$)$_2$:
bis(benzonitrile)-2,2'-bis(diphenylphosphino)-1,1'-binaphthylpalladium bis(tetrafluoroborate); and

[Pt(BINAP)(PhCN)$_2$](BF$_4$)$_2$:
bis(benzonitrile)-2,2'-bis(diphenylphosphino)-1,1'-binaphthylplatinum bis(tetrafluoroborate).

The transition metal complexes which are used in the present invention were synthesized according to known methods (S. G. Murray, et al., *J. Chem. Soc., Dalton Trans.*, pp.2246–2249 (1980), S. Oi, et al., *Tetrahedron Letters*, Vol. 37, pp. 6351–6354 (1996).

Reference Example 1

Synthesis of bis(benzonitrile)-1,4-bis(diphenylphosphino)butanepalladium bis(tetrafluoroborate); ([Pd(dppb)(PhCN)$_2$](BF$_4$)$_2$)

Under nitrogen, palladium chloride (455 mg, 2.56 mmol) and acetonitrile (25 ml) were placed in a round-bottomed flask equipped with a condenser, and refluxed under heat for one hour. While hot, the refluxed material was subjected to filtration, and the resultant filtrate was cooled to room temperature. After the substrate was cooled to room temperature, 1,4-bis-(diphenylphsphino)butane (1.09 g, 2.56 mmol) was added thereto. The mixture was refluxed with heat for a further two hours. Thereafter, the mixture was cooled to room temperature. Crystals were collected by filtration and dried under reduced pressure.

Under nitrogen, the palladium complex obtained from the above step, methylene chloride (35 ml), and benzonitrile (5 ml) were placed in a two-necked flask. To the mixture, a nitromethane (10 ml) solution of silver tetrafluoroborate (541 mg, 2.78 mmol) was added. The resultant mixture was stirred for three hours, to thereby precipitate silver chloride, which was separated by filtration. The filtrate was distillated under reduced pressure, and diethyl ether was added to the distilled product, to thereby precipitate crystals. The mixture containing the crystals were allowed to stand in a refrigerator over night, and resultant crystals were collected by filtration and dried under reduced pressure, to thereby obtain bis(benzonitrile)-1,4-bis(diphenylphosphino)butanepalladium bis(tetrafluoroborate) (2030 mg, 2.22 mmol, yield 89%).

$^1$H-NMR (400 MHz ; CDCl$_3$): 2.34(2H,broad), 2.91(4H, broad), 7.41~7.77 (30H, m)

Example 1

Synthesis of 4-cyclohexyl-2-oxetanone (R=a cyclohexyl group)

Under nitrogen, [Pd(dppb)(PhCN)$_2$](BF$_4$), (46.3 mg, 0.0507 mmol) obtained in Reference Example 1 was placed in a two-necked flask, and dry methylene chloride (20 ml) was added thereto to dissolve, followed by addition of cyclohexylaldehyde (117 mg, 1.04 mmol). To the resultant mixture, excess ketene gas (about 2.5 equivalents) was gradually introduced over five minutes at room temperature, followed by stirring for another one hour. The reaction was stopped by the addition of 1N HCl (10 ml), and the reaction product was taken up with methylene chloride (20 ml×5 times). The organic layer was washed with a saturated aqueous solution of NaCl (100 ml×1 time) and dried with sodium sulfate anhydrate. After filtration, the filtrate was concentrated, and subjected to gas chromatography (CROMPACK 0.25 mm ID×25 m; column temperature 135° C.; internal standard: n-butyl benzoate), to thereby quantitatively determine 4-cyclohexyl-2-oxetanone. The yield of 4-cyclohexyl-2-oxetanone was 98%.

The crude product was distilled (60° C., 0.15 mmHg) according to the Kugel Role method, to thereby obtain 4-cyclohexyl-2-oxetanone (128 mg, 0.83 mmol, yield 80%).

$^1$H-NMR (250 MHz ; CDCl$_3$): 0.96~1.05(2H, m), 1.19~1.32(3H, m), 1.58~1.82(5H, m), 1.97~2.08(1H, m), 3.11(1H, dd, J=16.2, 4.4 Hz), 3.42(1H, dd, J=16.2, 5.8 Hz), 4.16~4.24(1H, m) IR (neat) cm$^{-1}$: 1835

Example 2

Synthesis of 4-cyclohexyl-2-oxetanone (R=a cyclohexyl group)

Under nitrogen, [Pd(dppb)(PhCN)$_2$](BF$_4$)$_2$ (5.5 mg, 0.0060 mmol) obtained in Reference Example 1 was placed in a two-necked flask, and dry methylene chloride (20 ml) was added thereto to dissolve, followed by addition of cyclohexylaldehyde (117 mg, 1.04 mmol). To the resultant mixture, excess ketene gas (about 2.5 equivalents) was gradually introduced over five minutes at room temperature, followed by stirring for another one hour. The reaction was stopped by addition of 1N HCl (10 ml), and the reaction product was taken up with methylene chloride (20 ml×5 times). The organic layer was washed with a saturated aqueous solution of NaCl (100 ml×1 time) and dried with sodium sulfate anhydrate. After filtration, the filtrate was concentrated, and subjected to gas chromatography (CROMPACK 0.25 mm ID×25 m; column temperature 135° C.; internal standard: n-butylbenzoate), to thereby quantitatively determine 4-cyclohexyl-2-oxetanone. The yield of 4-cyclohexyl-2-oxetanone was 99%.

Example 3

Synthesis of 4-ethyl-2-oxetanone (R=an ethyl group)

Under nitrogen, [Pd(dppb)(PhCN)$_2$](BF$_4$)$_2$ (46.3 mg, 0.0507 mmol) obtained in Reference Example 1 was placed in a two-necked flask, and dry methylene chloride (20 ml) was added thereto to dissolve, followed by addition of propylaldehyde (60.9 mg, 1.05 mmol). To the resultant mixture, excess ketene gas (about 2.5 eqivalents) was gradually introduced over five minutes, followed by stirring for another one hour. To stop the reaction, 1N HCl (10 ml) was added, and the product was taken up with methylene chloride (20 ml×5 times). The organic layer was washed with a saturated aqueous solution of NaCl (100 ml×1 time) and dried with sodium sulfate anhydrate. After filtration, the filtrate was concentrated and subjected to gas chromatography (CROMPACK 0.25 mm ID×25 m; column temperature 135° C.; internal standard: n-butylbenzoate), to thereby quantitatively determine 4-ethyl-2-oxetanone. The yield of 4-ethyl-2-oxetanone was 99%.

The crude product was distilled according to the Kugel Roll method (60° C., 20 mmHg), to thereby obtain 4-ethyl-2-oxetanone.

$^1$H-NMR (250 MHz ; CDCl$_3$): 1.02(3H, t, J=7.4 Hz), 1.70~1.93 (2H, m), 3.06(1H, dd, J=16.3, 4.3 Hz), 3.58(1H, dd, J=16.3, 5.7 Hz). 4.40~4.50(1H, m) IR (neat) cm$^{-1}$:1821

Example 4

Synthesis of 4-n-hexyl-2-oxetanone (R=an n-hexyl group)

Under nitrogen, [Pd(dppb)(PhCN)$_2$](BF$_4$)$_2$ (46.3 mg, 0.0507 mmol) obtained in Reference Example 1, was placed in a two-necked flask, and dry methylene chloride (20 ml) was added thereto to dissolve, followed by addition of n-heptylaldehyde (118 mg, 1.04 mmol). To the resultant mixture, excess ketene gas (about 2.5 equivalents) was gradually introduced over five minutes, followed by stirring for another one hour. To stop the reaction, 1N HCl (10 ml) was added, and the product was taken up with methylene chloride (20 ml×5 times). The organic layer was washed with a saturated aqueous solution of NaCl (100 ml×1 time) and dried with sodium sulfate anhydrate. After filtration, the filtrate was concentrated and subjected to gas chromatography (CROMPACK 0.25 mm ID×25 m; column temperature 135° C.; internal standard: n-butylbenzoate), to thereby quantitatively determine 4-n-hexyl-2-oxetanone. The yield of 4-n-hexyl-2-oxetanone was 97%.

The crude product was distilled according to the Kugel Roll method (60° C., 5 mmHg), and 4-n-hexyl-2-oxetanone was obtained.

$^1$H-NMR (250 MHz ; CDCl$_3$): 0.89(3H, t, J=6.6 Hz), 1.30~1.46(8H, m), 1.63~1.91(2H, m), 3.06(1H, dd, J=16.3, 4.2 Hz), 3.52(1H, dd, J=16.3, 5.8 Hz), 4.47~4.56(1H, m) IR (neat) cm$^{-1}$: 1820

Example 5

Synthesis of 4-isopropyl-2-oxetanone (R=an isopropyl group)

Under nitrogen, [Pd(dppb)(PhCN)$_2$](BF$_4$)$_2$ (46.3 mg, 0.0507 mmol) obtained in Reference Example 1 was placed in a two-necked flask, and dry methylene chloride (20 ml) was added thereto to dissolve, followed by addition of 2-methylpropylaldehyde (65 mg, 1.04 mmol). To the resultant mixture, excess ketene gas (about 2.5 equivalents) was gradually introduced over five minutes, followed by stirring for another one hour. The reaction was stopped by addition of 1N HCl (10 ml), and the reaction product was taken up with methylene chloride (20 ml×5 times). The organic layer was washed with a saturated aqueous solution of NaCl (100 ml×1 time) and dried with sodium sulfate anhydrate. After filtration, the filtrate was concentrated and subjected to gas chromatography (CROMPACK 0.25 mm ID×25 m; column temperature 135° C.; internal standard: n-butylbenzoate), to thereby quantitatively determine 4-isopropyl-2-oxetanone. The yield of 4-isopropyl-2-oxetanone was 99%.

The crude product was distilled according to the Kugel Roll method (60° C., 10 mmHg), to thereby obtain 4-isopropyl-2-oxetanone.

$^1$H-NMR (250 MHz ; CDCl$_3$): 1.00(3H, d, J=6.7 Hz), 1.02(3H, d, J=6.7 Hz), 1.90~1.99(1H, m), 3.09(1H, dd, J=16.5, 4.4 Hz), 3.44(1H, dd, J=16.5, 5.8 Hz), 4.16~4.25 (1H, m) IR (neat) cm$^{-1}$: 1823

Example 6

Synthesis of 4-tert-butyl-2-oxetanone (R=a tert-butyl group)

Under nitrogen, [Pd(dppb)(PhCN)$_2$](BF$_4$)$_2$ (46.3 mg, 0.0507 mmol) obtained in Reference Example 1 was placed in a double-necked flask, and dry methylene chloride (20 ml) was added thereto to dissolve, followed by addition of 2,2-dimethylpropylaldehyde (90 mg, 1.05 mmol). To the resultant mixture, excess ketene gas (about 2.5 equivalents) was gradually introduced over five minutes, followed by stirring for another one hour. The reaction was stopped by addition of 1N HCl (10 ml), and the reaction product was taken up with methylene chloride (20 ml×5 times). The organic layer was washed with a saturated aqueous solution of NaCl (100 ml×1 time) and dried with sodium sulfate anhydrate. After filtration, the filtrate was concentrated and subjected to gas chromatography (CROMPACK 0.25 mm ID×25 m; column temperature 135° C.; internal standard: n-butylbenzoate), to thereby quantitatively determine 4-tert-butyl-2-oxetanone. The yield of 4-tert-butyl-2-oxetanone was 63%.

The crude product was distilled according to the Kugel Roll method (60° C., 10 mmHg), to thereby obtain 4-tert-butyl-2-oxetanone.

$^1$H-NMR (250 MHz ; CDCl$_3$): 0.99(9H, s), 3.15(1H, dd, J=16.4, 4.5 Hz), 3.42(1H, dd, J=16.4, 5.9 Hz), 4.20~4.27 (1H, m) IR (neat) cm$^{-1}$: 1831

Examples 7 to 18

Synthesis of 4-cyclohexyl-2-oxetanone (R=a cyclohexyl group)

The procedure of Example 1 was performed except that cyclohexylaldehyde was used as a reaction substrate and a variety of transition metal-phosphine complexes were used as catalysts at different reaction temperatures and with different solvents, to thereby synthesize 4-cyclohexyl-2-oxetanone. The reaction conditions and yield of 4-cyclohexyl-2-oxetanone are shown in Table 1.

TABLE 1

| Example | Transition metal-phosphine complex (4) | Amount of (4) (mol %) | Reaction time (hr) | Reaction temp. (° C.) | Solvent | Yield (%) |
|---|---|---|---|---|---|---|
| 7  | [Pd(PPh$_3$)$_2$(PhCN)$_2$](BF$_4$)$_2$ | 5  | 1 | −78        | CH$_2$Cl$_2$ | 33 |
| 8  | [Pd(dppe)(PhCN)$_2$](BF$_4$)$_2$       | 5  | 1 | −78        | CH$_2$Cl$_2$ | 46 |
| 9  | [Pd(dppp)(PhCN)$_2$](BF$_4$)$_2$       | 5  | 1 | −78        | CH$_2$Cl$_2$ | 55 |
| 10 | [Pd(dppb)(PhCN)$_2$](BF$_4$)$_2$       | 5  | 1 | −78        | CH$_2$Cl$_2$ | 65 |
| 11 | [Pd(dppf)(PhCN)$_2$](BF$_4$)$_2$       | 5  | 1 | −78        | CH$_2$Cl$_2$ | 56 |
| 12 | [Pd((s)-BINAP)(PhCN)$_2$](BF$_4$)$_2$  | 10 | 1 | −78        | CH$_2$Cl$_2$ | 75 |
| 13 | [Pd((s)-BINAP)(PhCN)$_2$](BF$_4$)$_2$  | 5  | 1 | Room temp. | PhMe         | 43 |
| 14 | [Pd(dppb)(PhCN)$_2$](BF$_4$)$_2$       | 5  | 1 | −40        | CH$_2$Cl$_2$ | 52 |
| 15 | [Pd(dppb)(PhCN)$_2$](BF$_4$)$_2$       | 5  | 1 | −40        | CHCl$_3$     | 50 |
| 16 | [Pd(dppb)(PhCN)$_2$](BF$_4$)$_2$       | 5  | 1 | 0          | CH$_2$Cl$_2$ | 97 |
| 17 | [Pd(dppb)(PhCN)$_2$](BF$_4$)$_2$       | 5  | 1 | 0          | CHCl$_3$     | 68 |
| 18 | [Pt((R)-BINAP)(PhCN)$_2$](BF$_4$)$_2$  | 10 | 1 | −78        | CH$_2$Cl$_2$ | 82 |

Example 19

Synthesis of 4-(2-phenylethyl)-2-oxetanone (R=a 2-phenylethyl group)

Under nitrogen, [Pd(dppb)(PhCN)$_2$](BF$_4$)$_2$ (70.0 mg, 0.0766 mmol) obtained in Reference Example 1 was placed in a sidearm flask, and dry methylene chloride (20 ml) was added thereto to dissolve, followed by addition of 3-phenylpropanal (203 mg, 1.52 mmol). To the resultant mixture, excess ketene gas (about 2.5 equivalents) was gradually introduced over five minutes at room temperature, followed by stirring for another one hour. The reaction was stopped by addition of 1N HCl (10 ml), and the product was taken up with methylene chloride (20 ml×5 times). The organic layer was washed with a saturated aqueous solution of NaCl (100 ml×1 time) and dried with sodium sulfate anhydrate. After filtration, the filtrate was concentrated and subjected to gas chromatography (CROMPACK 0.25 mm ID×30 m; column temperature 100–200° C.; temperature elevation rate 10° C./minute; internal standard: n-butylbenzoate), to thereby quantitatively determine 4-(2-phenylethyl)-2-oxetanone. The yield of 4-(2-phenylethyl)-2-oxetanone was 88%.

The crude product was purified through use of silica gel chromatography (ethyl acetate: n-hexane=2: 3), to thereby obtain 4-(2-phenylethyl)-2-oxetanone (165 mg, 0.94 mmol, yield: 62%).

$^1$H-NMR (250 MHz ; CDCl$_3$): 2.04~2.22(2H,m), 2.71~2.84(2H, m), 3.02(1H, dd, J=16.2, 4.2 Hz), 3.47(1H, dd, J=16.3, 5.9 Hz), 4.47~4.57(1H, m), 7.17~7.32(5H, m) IR (neat) cm$^{-1}$: 1824

Example 20

Synthesis of 4-vinyl-2-oxetanone (R=a vinyl group)

Under nitrogen, [Pd(dppb)(PhCN)$_2$](BF$_4$)$_2$ (140.0 mg, 0.153 mmol) obtained in Reference Example 1, was placed in a sidearm flask, and dry methylene chloride (20 ml) was added thereto to dissolve, followed by addition of acrylaldehyde (172 mg, 3.06 mmol). To the resultant mixture, excess ketene gas (about 2.5 equivalents) was gradually introduced over ten minutes at room temperature, followed by stirring for another one hour. The reaction was stopped by the addition of 1N HCl (20 ml), and the product was taken up with methylene chloride (40 ml×5 times). The organic layer was washed with a saturated aqueous solution of NaCl (200 ml×1 time) and dried with sodium sulfate anhydrate. After filtration, the filtrate was concentrated and subjected to gas chromatography (CROMPACK 0.25 mm ID×30 m; column temperature 100–200° C.; temperature elevation rate 10° C./minute; internal standard: n-butyl benzoate), to thereby quantitatively determine 4-vinyl-2-oxetanone. The yield of 4-vinyl-2-oxetanone was 95%.

The crude product was purified through use of silica gel chromatography (chloroform), to thereby obtain 4-vinyl-2-oxetanone (110 mg, 1.13 mmol, yield: 37%).

$^1$H-NMR (250 MHz ; CDCl$_3$): 3.21(1H, dd, J=16.5, 4.5 Hz), 3.66(1H, dd, J=16.4, 6.0 Hz), 4.87~4.96(1H, m), 5.39 (1H, d, J=10.4 Hz), 5.49(1H, d, J=17.0 Hz), 5.93~6.10(1H, m) IR (neat) cm$^{-1}$: 1828, 1651

Japanese Patent Application No. 10-059522 filed on Mar. 11, 1998, is incorporated herein by reference in its entirety.

What is claimed is:

1. A process for producing a β-lactone compound having the formula (3):

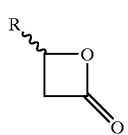

(3)

wherein R represents C1–C15 alkyl, which is optionally substituted by aryl, C2–C15 alkenyl, 5–7 membered alicyclic, or phenyl, which is optionally substituted by C1–C4 alkyl; which process comprises:

reacting an aldehyde having the formula (1):

RCHO     (1)

wherein R is the same as defined above; with a ketene having the formula (2):

$CH_2$=C=O     (2)

in the presence of, as a catalyst, a transition metal-phosphine complex.

2. The process of claim 1, wherein the transition metal-phosphine complex is a palladium-phosphine complex or a platinum phosphine complex.

3. The process of claim 1, wherein the transition metal-phosphine complex has the formula (4):

$$[ML_nX_2]Y_2 \qquad (4)$$

wherein M is palladium or platinum; L is a tertiary phosphine; X is a C1–C5 alkylnitrile, benzonitrile, phthalonitrile, pyridine, dimethyl sulfoxide, N,N-dimethylformamide, or acetone; Y is halogen, $BF_4$, $ClO_4$, $CF_3SO_3$, $PF_6$, or $BPh_4$; Ph is phenyl; and n is 2, when L is a monodentate phosphine ligand, and 1 when L is a bidentate phosphine ligand.

4. The process of claim 2, wherein the transition metal-phosphine complex has the formula (4):

$$[ML_nX_2]Y_2 \qquad (4)$$

wherein M is palladium or platinum; L is a tertiary phosphine; X is C1–C5 alkylnitrile, benzonitrile, phthalonitrile, pyridine, dimethylsulfoxide, N,N-dimethylformamide, or acetone; Y is halogen, $BF_4$, $ClO_4$, $CF_3SO_3$, $PF_6$, or $BPh_4$; Ph represents phenyl; and n is 2, when L is a monodentate phosphine ligand, and 1 when L is a bidentate phosphine ligand.

* * * * *